United States Patent [19]
Dazens et al.

[11] Patent Number: 5,650,462
[45] Date of Patent: Jul. 22, 1997

[54] COMPOSITE MATERIAL HAVING A FIBROUS REINFORCEMENT AND MATRIX OBTAINED BY THE POLYMERIZATION OF ACRYLIC MONOMERS AND ITS PRODUCTION

[75] Inventors: Véronique Dazens, Pyla Sur Mer; Daniel Beziers; Evelyne Chataignier, both of St. Medard en Jalles; Claude Filliatre, Talence; Jean-Jacques Villenave, Gradignan; Christian Servens, St. Aubin de Medoc, all of France

[73] Assignee: Societe Nationale Industrielle et Aerospatiale, Paris Cedex, France

[21] Appl. No.: 714,977

[22] Filed: Sep. 17, 1996

[30] Foreign Application Priority Data

Sep. 20, 1995 [FR] France ..................... 95 11038

[51] Int. Cl.$^6$ .................................................. C08L 31/00
[52] U.S. Cl. ............................................. 524/558; 526/320
[58] Field of Search ............................ 524/558; 526/320

[56] References Cited

U.S. PATENT DOCUMENTS 3,586,527  6/1971  Aronoff et al. .
3,721,644  3/1973  Stoffey et al. .
3,835,090  9/1974  Gander et al. .

OTHER PUBLICATIONS

Document 122:326701 "Polymer dispersion type liquid crystal composite layer, its manufacture, and high contrast optical device using same" Kita et al JP07028040, 1995 Jan. 31 in–house abstract pp. 46 and 47.

Patent Abstracts of Japan, vol. 9, No. 119, May 23, 1985, and JP–A–60 011409, Jan. 21, 1985.

*Primary Examiner*—Joseph L. Schofer
*Assistant Examiner*—N. Sarofim
*Attorney, Agent, or Firm*—Oblon, Spivak, McClelland, Maier & Neustadt, P.C.

[57] ABSTRACT

The invention relates to the production of composite materials having a fibrous reinforcement and matrix obtained by the polymerization of acrylic monomers.

These acrylic monomers are tetraacrylates of formula:

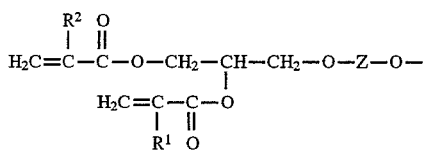

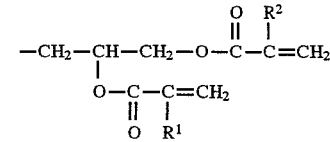

in which $R^1$ and $R^2$, which can be the same or different, represent H or $CH_3$, and Z is a divalent group having 1 or 2 aromatic or aliphatic cycles.

For example, Z is a group derived from bisphenol A and $R^1$ and $R^2$ represent H.

The composite materials can be prepared by injection moulding.

15 Claims, No Drawings

COMPOSITE MATERIAL HAVING A FIBROUS REINFORCEMENT AND MATRIX OBTAINED BY THE POLYMERIZATION OF ACRYLIC MONOMERS AND ITS PRODUCTION

DESCRIPTION

The present invention relates to the use of acrylic monomers for forming the matrix of composite materials having a fibrous reinforcement.

It more particularly applies to the production of composite materials intended for the aviation sector, which must have ageing properties in a humid atmosphere corresponding to avionics standards. Composite materials of this type generally have a fibrous reinforcement e.g. constituted by fibres of carbon, glass, aramide, e.g. Kevlar, coated in an organic resin matrix. For the preparation of the material, the fibrous reinforcement is generally impregnated with the resin in the liquid state, followed by the hardening of the resin. Resins which can be hardened by X-rays or electrons, i.e. polymerizable by ionization, are of particular interest for producing such materials, because they harden rapidly, virtually without any temperature rise. This obviates treatment conditions which could be prejudicial to the quality of the composite.

Among the resins usable for forming the matrix of such materials, acrylic resins are advantageous, because they are polymerizable by ionization and have good thermal properties.

Thus, FR-A-2 581 991, FR-A-2 594 825 and EP-A-218 722, disclose polymerizable compositions based on triacrylic, tetraacrylic or methacrylic monomers, which permit the obtaining of three-dimensional polymers in highly cross-linked form and with good thermal performance characteristics. These monomers are obtained by reacting an aromatic or cycloaliphatic diamine with glycidyl methacrylate or acrylate. Such compositions are not suitable for the preparation of composite materials having to withstand ageing in a humid atmosphere, because their structure contains hydrophilic functions (amine and hydroxyl groups), which are liable to bring about a drop in the thermal properties following ageing in a humid atmosphere. Moreover, the presence of such functions leads to an increase in the viscosity of the monomers, which is a disadvantage for their introduction to a fibrous reinforcement. Moreover, it is necessary in certain cases to carry out a subsequent heat treatment in view of an incomplete polymerization of the matrix, which does not make it possible to fully profit from the advantages (speed and ease of operation) of polymerization by ionization.

The present invention specifically relates to a composite material having a fibrous reinforcement and a matrix obtained by the polymerization of acrylic or methacrylic monomers hardenable under X-radiation or electrons obviating, these disadvantages and making it possible to obtain a composite material having the desired resistance to ageing in a humid atmosphere (little absorption of water whilst maintaining a high glass transition point (Tg) of approximately 120° to 170° C.).

The invention therefore relates to a composite material comprising a fibrous reinforcement and a matrix obtained by the polymerization of a composition hardenable by ionization by means of X-rays or electrons, constituted by a mixture of a tetraacrylate of formula:

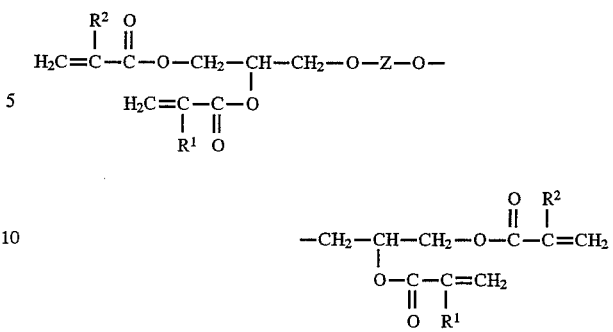

in which and $R^1$ and $R^2$, which can be the same or different, represent H or $CH_3$, and Z is a divalent group having one or two aromatic or aliphatic cycles, with 1) a diacrylate and/or triacrylate of formula:

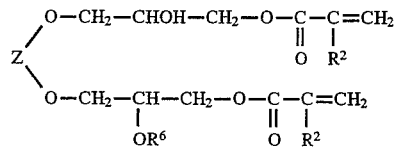

in which Z and $R^2$ have the meanings given hereinbefore and $R^6$ represents H or the group of formula:

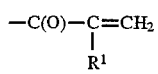

in which $R^1$ represents H or $CH_3$, or 2) a monofunctional acrylic diluent.

It is pointed out that in the present text the term acrylate also applies to methacrylate.

In the composition material according to the invention, the fibrous reinforcement can be formed by fibres of carbon, glass or aramide, such as Kevlar.

This fibrous reinforcement can be in different forms, e.g. in the form of stacked fibres, bidirectional sheets or tridirectional or multidirectional fabrics.

Generally, this fibrous reinforcement represents 55 to 75 vol. % of the composite material, the remaining 25 to 45% being occupied by the hardened acrylic resin matrix.

It is in particular possible to produce a composite material having 70 vol. % fibrous reinforcement and 30 vol. % resin.

The tetraacrylates used in the invention are particularly interesting, because they have four acrylic reactive functions permitting the obtaining of a high polymer network crosslinking density, so as to increase the glass transition point (Tg) of the material. Moreover, they incorporate no hydrophilic function (hydroxyl or amine) liable to weaken the behaviour of the material in a humid atmosphere.

In these tetraacrylates, the central part constituted by the Z group can be of different types, e.g. formed by a linkage:

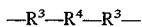

in which $R^4$ is a divalent group, e.g.

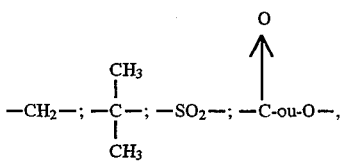

and the $R^3$ are aromatic cycles.

The Z group can also be constituted by a single aromatic or aliphatic cycle such as:

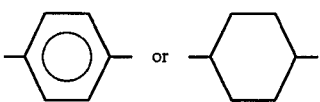

According to a preferred embodiment of the invention, the Z group of the tetraacrylate is derived from bisphenol A or bisphenol F. In this case, Z complies with the formula:

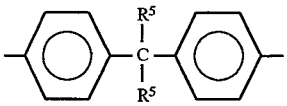

in which $R^5$ represents a hydrogen atom or a methyl group.

These tetraacrylic monomers can be obtained from diacrylates of formula:

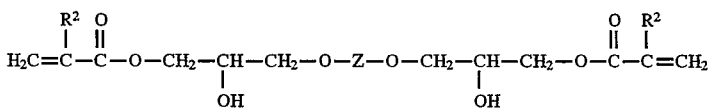

called BIS-GA or BIS-GA (methacrylate), by reacting them with an acid chloride of formula:

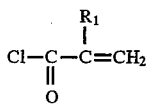

in which $R^1$, $R^2$ and Z have the meanings given hereinbefore.

This reaction can be performed in a single stage in a basic medium, e.g. in the presence of a tertiary amine such as triethyl amine. Working generally takes place in an organic solvent such as chloroform. During this reaction, several products can be formed and are constituted by the tetraacrylic monomer and the triacrylic monomer.

By varying the experimental conditions, the relative diacrylate and acid chloride quantities, it is possible to control the synthesis and orient it either towards the production of the pure tetraacrylic product without subsequent purification, or to the obtaining of a mixture of triacrylic and tetraacrylic products. This latter possibility is of interest because, as will be shown hereinafter, it makes it possible to directly obtain hardenable compositions suitable for producing the matrix of a composite material.

The starting diacrylates used for the synthesis of the tetraacrylate can be obtained from the glycidyl ether of the corresponding diol HO—Z—OH by reaction with acrylic or methacrylic acid. Thus, in the case where Z represents bisphenol A derivatives, said diacrylate or epoxy acrylate, which is a commercial product, is formed from the glycidyl ether of bisphenol A and acrylic or methacrylic acid.

The tetraacrylates used in the invention are of interest due to their low viscosity and their capacity to be hardened by X-rays or electrons, at the standard doses (50 to 250 kGy) whilst giving a hardened material with a high glass transition point (Tg), which can reach 250° C.

However, although it leads to interesting properties, the monomer in the pure state has the disadvantage of becoming fragile after hardening.

Moreover, according to the invention, preference is given to the mixing thereof with a monofunctional acrylic diluent or with the aforementioned diacrylates and/or triacrylates, in order to flexibilize it without decreasing its resistance to ageing in a humid atmosphere.

The hardenable compositions can also comprise one or more other additives chosen from among thickening agents, fillers, dyes, rubbers and vinyl termination butadienes (VTBN). These additives can be used for regulating the viscosity of the monomer or improving the properties of the hardened resin.

Tetraacrylate in the pure state has a very low viscosity, which can be of interest for producing parts by injection moulding, but which is not suitable for producing a preimpregnated fibrous reinforcement. In the latter case, it is necessary to thicken the formulation by adding a thickener. The latter can be a thermoplastic material or a thixotropic agent, such as silica gel. It is also possible to add additives for improving the mechanical properties of the material and in particular increasing its cracking resistance. Additives of this type can be constituted by a vinyl termination butadiene (VTBN) or a rubber.

The hardenable compositions constituted by a mixture of the tetraacrylate monomer with the corresponding diacrylate and/or triacrylate can be directly obtained during the synthesis of the tetraacrylate, as was shown hereinbefore, by appropriately regulating the reaction conditions.

For the diacrylate-tetraacrylate compositions, these can be obtained by mixing them in the desired proportions.

In the case of hardenable compositions based on tetraacrylate and diacrylate and/or triacrylate, the tetraacrylate content must be adequate to obtain the desired thermal properties. In general, these compositions have at least 50 wt. % tetraacrylate.

When using an acrylic diluent in the hardenable compositions according to the invention, the latter is chosen as a function of its hardened resin flexibilizing properties, but it must decrease the Tg in acceptable proportions for the desired properties and have a good miscibility with the tetraacrylate. This diluent preferably comprises one or more aromatic or aliphatic cycles and a single acrylic function. Among the monofunctional acrylic diluents of this type, reference can be made to isobornyl monoacrylate.

However, it is also possible to use other acrylic diluents, e.g. hexane diol diacrylate and tripropylene glycol diacrylate.

Generally, said acrylic diluent represents 30 to 50 and preferably 30 to 40 wt. % of the composition.

The hardenable compositions can be used for the preparation of composite materials by injection moulding.

In this case, the process for the production of the composite material consists of placing a fibrous reinforcement in a mould, injecting under pressure into said mould the aforementioned hardenable composition and then subjecting the mould filled with the composition to an ionization by means of X-rays or electrons in order to harden said composition.

Ionization doses of 50 to 250 and preferably 100 to 150 kGy are suitable for this purpose. Generally ionization takes place under an inert atmosphere, e.g. under nitrogen.

Although the acrylic resins used in the invention are more particularly suitable for producing materials by injection moulding, they can also be used for producing composite materials by other methods, e.g. by that using a preimpregnated fibrous reinforcement, in the form of coated fibres or preimpregnated fabrics or sheets, which are brought into the desired form by heating and which are then hardened by ionization using X-rays or electrons.

In this case, use is made of a composition incorporating a thickener for preparing the preimpregnated product.

Other features and advantages of the invention can be gathered from the following non-limitative, illustrative, exemplified description.

EXAMPLE 1

Tetraacrylate

1) Preparation

During synthesis, two products are formed in accordance with the following reaction diagrams:

degassing in vacuum and subjecting the thus prepared samples to the action of an electron beam produced by an accelerator.

The ionization conditions are:
power: 20 kW
mean energy of the beam: 10 MeV
atmosphere: nitrogen
dose: 150 to 250 kGy.

This gives hardened samples and the glass transition points (Tg) thereof are determined. The results obtained as a function of the dose are given in table 1.

TABLE 1

| Monomer | Dose (kGy) | Tg (°C.) |
|---|---|---|
|  | 150 | 210 |
| pure | 200 | 230 |
| tetraacrylate | 250 | 248 |

The Tg values obtained are high, no matter what the dose used. Moreover, in all cases, the action of a subsequent heat treatment leads to no improvement in the properties of the materials, which indicates that they are appropriately polymerized.

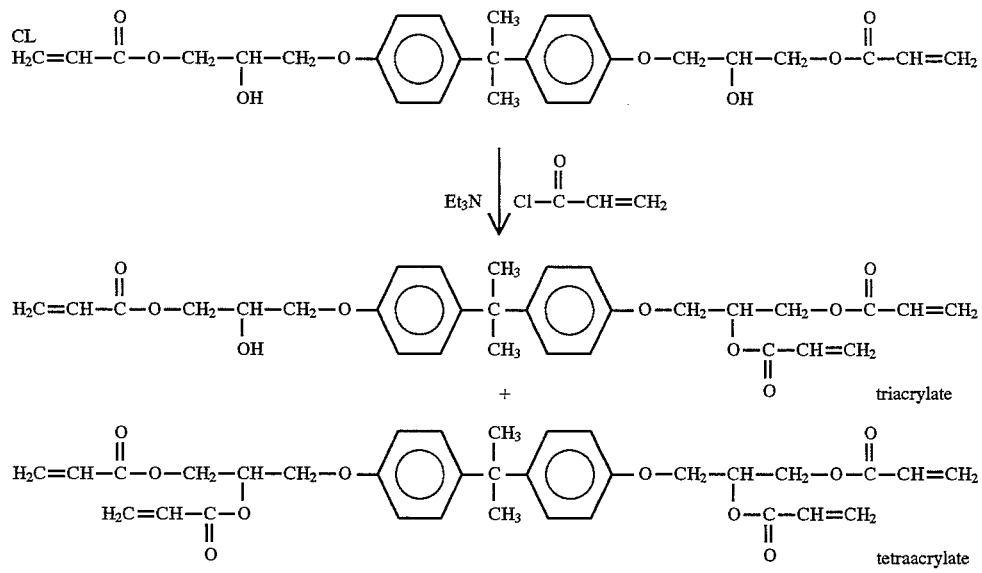

However, it is possible to obtain the pure tetraacrylate by modifying the reagent quantities used (table 2).

In a 500 ml three-necked flask, the Bis-Ga resin (0.1 mole) dissolved in 300 ml of anhydrous chloroform is mixed with triethyl amine (0.4 mole) in 150 ml of anhydrous chloroform. The system is placed under an inert atmosphere (nitrogen scavenging). The acryloyl chloride (0.37 mole) in 150 ml of anhydrous chloroform is added rapidly at ambient temperature in order to obtain the pure tetraacrylic compound. When working takes place slowly, a mixture of triacylate and tetraacrylate is obtained and the addition speed is determined on the proportions of the products formed. The mixture is stirred for 20 hours. The solution turns yellow. The triethyl amine seal formed during the reaction precipitates in the medium when ether is poured onto the solution. After filtering and evaporating the solvents, the resin obtained is the tetraacrylate.

2) Hardening.

The previously obtained tetraacrylate is e.g. placed in open, parallel-epipedic moulds (100/40/2 mm), followed by The mechanical characteristics of the hardened samples are as follows:

modulus: 3700 MPa breaking stress: 45 MPa percentage elongation: 1.2%.

These materials formed from tetraacrylate in the pure state consequently have good properties. However, due to their high rigidity, fractures can occur during ageing in a humid atmosphere. It is therefore preferable to dilute the tetraacrylate with another acrylic monomer in order to flexibilize it.

EXAMPLES 2 TO 5

Hardenable Compositions Based on Mixtures of Tetraacrylate and Diacrylate or Triacrylate The compositions of examples 2 to 5 are given in table 2. The compositions of examples 4 and 5 are obtained by mixing the tetraacrylate prepared in example 1 with the corresponding diacrylate in the proportions indicated in table 2.

The compositions of examples 2 and 3 are obtained directly by synthesis working as in example 1, but using the reagent quantities given in table 3 and slowly adding the acryloyl chloride.

The compositions undergo hardening as in example 1, using an ionization dose of 100 or 150 kGy. The characteristics of the hardened products obtained are given in table 2.

TABLE 2

| Ex. | Composition (wt. %) | Dose (kGy) | Tg °C. | Modulus (MPa) | Elongation % |
|---|---|---|---|---|---|
| 1 | Pure tetraacylate | 150 | 210 | 3700 | 1.2 |
| 2 | Tetraacrylate[1]-triacylate[2] 90%   10% | 150 | 160 | 3300 | 1.6 |
| 3 | Tetraacylate[1]-triacylate[2] 80%   20% | 150 | 150 | 3700 | 1.6 |
| 4 | Tetraacylate[1]-diacrylate[3] 50%   50% | 100 | 173 | / | / |
| 5 | Tetraacylate[1]-diacrylate[3] 25%   75% | 100 | 170 | / | / |

[1]Tetraacrylate of example 1
[2]Triacrylate with the formula given in example 1
[3]Diacrylate of bis-GA with the formula given in example 1.

Tetraacrylate of example 1
Triacrylate with the formula given in example 1.
Diacrylate of bis-Ga with the formula given in example 1.

TABLE 3

| Ex | Formulation | Reagents | Number of moles |
|---|---|---|---|
| 1 | Pure tetraacrylic | bis-GA | 0.1 |
|   |   | acryloyl chloride | 0.37 |
|   |   | triethyl amine | 0.4 |
| 2 | Tetra(90)/triacrylate(10) | bis-GA | 0.1 |
|   |   | acryloyl chloride | 0.32 |
|   |   | trimethyl amine | 0.34 |
| 3 | Tetra(80)/triacylate(20) | bis-GA | 0.1 |
|   |   | acryloyl chloride | 0.28 |
|   |   | triethyl amine | 0.3 |

With respect to table 2, it can be seen that the addition of diacrylate or triacylate leads to flexibilization, but decreases the glass transition temperature.

EXAMPLES 6 TO 9

Hardenable Compositions Based on Tetraacrylate and a Monoacrylic Diluent

These examples use the tetraacrylate of example 1 and a reactive diluent constituted by isobornyl monoacrylate in a proportion such that it represents 10, 20, 30 or 40 wt. % of the composition.

On the basis of these compositions, hardened products are produced following the same operating procedure as in example 1 and using a dose of 150 kGy.

The glass transition point (Tg) of the products obtained after hardening and the characteristics (Tg and % water absorbed) obtained after ageing the hardened product in a humid atmosphere are given in table 4.

Ageing in a humid atmosphere takes place in accordance with avionics standard SACMA SRM 11-88. It consists of immersing samples of hardened materials in distilled water at 70° C. for 336 hours.

TABLE 4

| Ex | Hardenable composition | AIB* content (wt. %) | Dose (kGy) | Tg (°C.) | Tg after aging (°C.) | % absorbed water |
|---|---|---|---|---|---|---|
| 6 | tetraacrylate + isobornyl acrylate | 10 | 150 | 65 and 190 | material deteriorated | material deteriorated |
| 7 | tetraacrylate + isobornyl acrylate | 20 | 150 | 200 | material deteriorated | material deteriorated |
| 8 | tetraacrylate + isobornyl acrylate | 30 | 150 | 195 | 180 | 3.4 |
| 9 | tetraacrylate + isobornyl acrylate | 40 | 150 | 205 | 190 | 2.5 |

*AIB = isobornyl acrylate.

The results of this table show that it is appropriate to use at least 30% monoacrylic diluent for obtaining a healthy material after wet ageing. The glass transition points of the hardened materials are approximately 200° C. and the absorbed water percentages during ageing in a humid atmosphere are approximately 2%, being lower than those of epoxy acrylic resins which, in general, absorb about 5% water.

EXAMPLES 10 TO 12

Hardenable Compositions With Monoacrylic Diluents

These examples follow the same operating procedure as in examples 6 to 9 for preparing hardened materials from hardenable compositions containing 30, 35 or 40 wt. % isobornyl acrylate (AIB) and the doses given in the following table 5. In table 5 are also given the mechanical properties of the hardened products.

TABLE 5

| Ex | Formulation (wt. %) | Dose (kGy) | Modulus (MPa) | Maximum stress (MPa) | Elongation (%) |
|---|---|---|---|---|---|
| 10 | Tetra + AIB* 70 – 30 | 150 | 3500 | 42 | 1.2 |
| 11 | Tetra + AIB* 65 – 35 | 150 | 3700 | 72 | 2 |
| 12 | Tetra + AIB* 60 – 40 | 150 | 3500 | 63 | 1.7 |

*AIB = isobornyl acrylate.

Thus, these compositions make it possible to produce a composite material matrix having adequate characteristics.

EXAMPLES 13 TO 18

Composition Materials

In these examples preparation takes place of composite materials from a fibrous reinforcement constituted by carbon fabrics placed in a mould, impregnated with a hardenable composition having the formulation given in table 6 and then hardened in vacuum by ionization using electrons and the dose indicated in table 6.

The glass transition points (Tg) before and after ageing the material in a humid atmosphere are in accordance with avionics standard SACMA/SRM11-88 and are given in table 8.

TABLE 6

| Ex | Hardenable composition | Dose (kGy) | Tg (°C.) | Tg after ageing (°C.) |
|---|---|---|---|---|
| 13 | Tetraacrylate + 30% AIB* | 100 | 240 | 252 |
| 14 | Tetraacrylate + 30% ATB | 150 | 236 | 253 |
| 15 | Tetraacrylate + 35% AIB | 100 | 245 | 244 |
| 16 | Tetraacrylate + 35% AIB | 150 | 250 | 250 |
| 17 | Tetraacrylate + 40% AIB | 100 | 238 | 246 |
| 18 | Tetraacrylate + 40% AIB | 150 | 242 | 244 |

*AIB = isobornyl acrylate.

The results of table 6 confirm the obtaining of materials having glass transition points above 200° C. and which in a humid atmosphere will have a behaviour complying with aeronautical requirements.

Moreover, on comparing these results with those of tables 3 and 4, it can be seen that the Tg values of the composite materials are superior to those of hardened, resin only compositions. This confirms the interest of the compositions, which are sufficiently reactive to give their properties to a material in which they only represent 30 vol. %.

We claim:

1. Composite material comprising a fibrous reinforcement and a matrix obtained by the polymerization of a composition hardenable by ionization by means of X-rays or electrons, constituted by a mixture of a tetraacrylate of formula:

$$H_2C=C-C-O-CH_2-CH-CH_2-O-Z-O-$$
with $R^2$, $O$ substituents and $H_2C=C-C-O$ branch with $R^1$, $O$ $$-CH_2-CH-CH_2-O-C-C=CH_2$$
with $O$, $R^2$ and $O-C-C=CH_2$ branch with $O$, $R^1$ in which $R^1$ and $R^2$, which can be the same or different, represent H or $CH_3$, and Z is a divalent group having one or two aromatic or aliphatic cycles, with 1) a diacrylate and/or triacrylate of formula:

$$Z\begin{cases} O-CH_2-CHOH-CH_2-O-C-C=CH_2 \\ O-CH_2-CH-CH_2-O-C-C=CH_2 \end{cases}$$
with $OR^6$ and $O$, $R^2$ substituents in which Z and $R^2$ have the meanings given hereinbefore and $R^6$ represents or the group of formula:

$$-C(O)-C=CH_2$$
$$\phantom{-C(O)-}R^1$$

in which $R^1$ represents H or $CH_3$, or 2) a monofunctional acrylic diluent.

2. Material according to claim 1, characterized in that the reinforcement is formed from carbon fibres, glass fibres or aramide fibres.

3. Composite material according to either of the claims 1 and 2, characterized in that the fibrous reinforcement represents 55 to 75 vol. % of the material.

4. Composite material according to any one of the claims 1 to 3, characterized in that, in the formula of the tetraacrylate, Z represents a group of formula:

$$-R^3-R^4-R^3-$$

in which $R^4$ represents:

$$-CH_3-;\ -\underset{CH_3}{\overset{CH_3}{\underset{|}{\overset{|}{C}}}}-;\ SO_2;\ -CO-\ \text{or}\ -C-$$

and the $R^3$ are aromatic cycles.

5. Composite material according to claim 4, characterized in that Z represents a group of formula:

[structure: two phenyl rings connected by C with $R^5$ substituents]

in which $R^5$ represents a hydrogen atom or a methyl group.

6. Material according to any one of the claims 1 to 3, characterized in that the tetraacrylate complies with the formula:

[tetraacrylate structural formula]

7. Material according to any one of the claims 1 to 6, characterized in that the acrylic diluent is isobornyl monoacrylate.

8. Process for the preparation of a composite material, characterized in that it consists of placing a fibrous reinforcement in a mould, injecting under pressure into said mould a hardenable composition constituted by a mixture of a tetracrylate of formula:

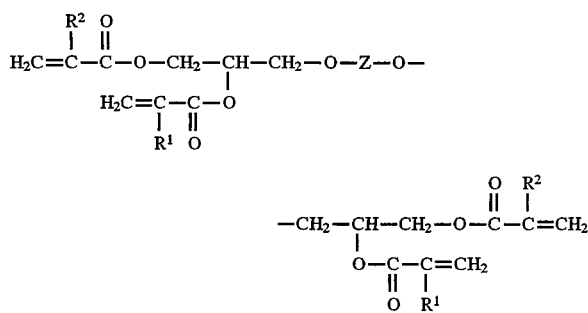

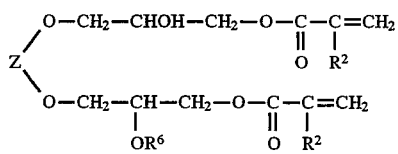

in which $R^1$ and $R^2$, which can be the same or different, represent H or $CH_3$, and Z is a divalent group having 1 or 2 aromatic or aliphatic cycles, with 1) a diacrylate and/or triacrylate of formula:

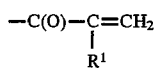

in which Z and $R^2$ have the meanings given hereinbefore and $R^6$ represents H or the group of formula:

—C(O)—C(R¹)=CH₂ in which $R^1$ represents H or $CH_3$, or 2) a monofunctional acrylic diluent, and then subjecting the mould filled with the composition to an ionization by means of X-rays or electrons in order to harden the composition.

9. Process according to claim 8, characterized in that the hardenable composition is a mixture of tetraacrylate and a monofunctional acrylic diluent and in that it comprises 50 to 70 wt. % tetraacrylate.

10. Process according to claim 8 or 9, characterized in that the monofunctional diluent is isobornyl monoacrylate.

11. Process according to claim 8, characterized in that the composition is a mixture of tetraacrylate and diacrylate and/or triacrylate and in that it comprises at least 50 wt. % tetraacrylate.

12. Process according to any one of the claims 8 to 11, characterized in that the hardenable composition also comprises one or more additives chosen from among thickening agents, fillers, dyes, rubbers and vinyl termination butadienes.

13. Process according to any one of the claims 8 to 12, characterized in that, in the formula of the tetraacrylate, Z represents a group of formula:

—R³—R⁴—R³— in which $R^4$ represents:

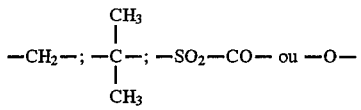

and the $R^3$ are aromatic cycles.

14. Process according to claim 13, characterized in that Z represents a group of formula:

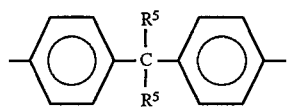

in which $R^5$ represents a hydrogen atom or a methyl group.

15. Process according to claim 14, characterized in that the tetraacrylate is in accordance with the formula:

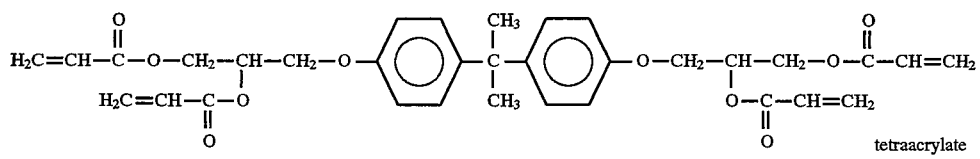

UNITED STATES PATENT AND TRADEMARK OFFICE
CERTIFICATE OF CORRECTION

PATENT NO.    : 5,650,462
DATED         : July 22, 1997
INVENTOR(S)   : Véronique DAZENS, et al.

It is certified that error appears in the above-indentified patent and that said Letters Patent is hereby corrected as shown below:

On the title page, Item [73], the Assignee should read:

--Assignee:   AEROSPATIALE Societe Nationale Industrielle,
              Paris Cedex, France--

Signed and Sealed this

Seventh Day of October, 1997

Attest:

BRUCE LEHMAN

*Attesting Officer*    *Commissioner of Patents and Trademarks*